US009422583B2

(12) United States Patent
Montelione et al.

(10) Patent No.: US 9,422,583 B2
(45) Date of Patent: Aug. 23, 2016

(54) STEREOSPECIFIC CARBONYL REDUCTASES

(71) Applicants: RUTGERS, THE STATE UNIVERSITY OF NEW JERSEY, New Brunswick, NJ (US); JIANGNAN UNIVERSITY, Wuxi (CN)

(72) Inventors: Gaetano T. Montelione, New Brunswick, NJ (US); Rong Xiao, New Brunswick, NJ (US); Yao Nie, Wuxi (CN); Yan Xu, Wuxi (CN)

(73) Assignees: Rutgers, The State University of New Jersey, New Brunswick, NJ (US); Jiangnan University, Wuxi (CN)

( * ) Notice: Subject to any disclaimer, the term of this patent is extended or adjusted under 35 U.S.C. 154(b) by 0 days.

(21) Appl. No.: 14/635,860

(22) Filed: Mar. 2, 2015

(65) Prior Publication Data

US 2015/0167032 A1 Jun. 18, 2015

Related U.S. Application Data

(62) Division of application No. 13/379,942, filed as application No. PCT/US2010/039666 on Jun. 23, 2010, now abandoned.

(60) Provisional application No. 61/219,610, filed on Jun. 23, 2009.

(51) Int. Cl.
| | |
|---|---|
| *C12P 7/62* | (2006.01) |
| *C12N 9/04* | (2006.01) |
| *C12P 7/04* | (2006.01) |
| *C12P 7/22* | (2006.01) |
| *C12P 41/00* | (2006.01) |

(52) U.S. Cl.
CPC .................. *C12P 7/62* (2013.01); *C12N 9/0006* (2013.01); *C12P 7/04* (2013.01); *C12P 7/22* (2013.01); *C12P 41/002* (2013.01); *Y02P 20/52* (2015.11)

(58) Field of Classification Search
CPC .............................. C12N 9/0006; C12P 7/04
USPC .................................................. 435/135, 189
See application file for complete search history.

(56) References Cited

U.S. PATENT DOCUMENTS

2009/0029430 A1* 1/2009 Kizaki ................. C12N 9/0006
435/155
2012/0270285 A1 10/2012 Montelione et al.

FOREIGN PATENT DOCUMENTS

CN 1884502 A 12/2006

OTHER PUBLICATIONS

Zhang et al. Protein Science (2008).*
Accession No. B2KJ46—Jun. 10, 2008.
Acton et al., "Robotic Cloning and Protein Production Platform of the Northeast Structural Genomics Consortium", *Methods Enzymol.* 394, 210-243 (2005).
Altschul et al., "Basic Local Alignment Search Tool", *J. Mol. Biol.*, 215, 403-410 (1990).
Bradshaw et al., "*Lactobacillus kefir* Alcohol Dehydrogenase: A Useful Catalyst for Synthesis", *J. Org. Chem. 57*, 1526-1532 (1992).
Bradshaw et al., "A *Pseudomonas* sp. Alcohol Dehydrogenase with Broad Substrate Specificity and Unusual Stereospecificity for Organic Synthesis", *J. Org. Chem.* vol. 57 (5), 1526-1532 (1992).
Corpet, "Multiple sequence alignment with hierarchical clustering", *Nucl. Acids Res.*, 16 (22), 10881-10890 (1988).
De Melis et al., "Isolation and characterization of a cDNA clone encoding cinnamyl alcohol dehydrogenase in Eucalyptus globulus Labill", *Plant Science* 143, 173-182 (1999).
De Wildeman et al., "Biocatalytic Reductions: From Lab Curiosity to "First Choice"", *Acc. Chem. Res. 40*, 1260-1266, (2007).
Engelking et al., "Stereoselective reduction of ethyl 4-chloro acetoacetate with recombinant *Pichia pastoris*", *Tetrahedron: Asymmetry 15*, 3591-3593 (2004).
Ernst et al., "Enantioselective reduction of carbonyl compounds by whole-cell biotransformation, combining a formate dehydrogenase and a (R)-specific alcohol dehydrogenase", *Appl. Microbiol. Biotechnol. 66*, 629-634 (2005).
Fantin et al., "Anti-Prelog Microbial Reduction of Prochiral Carbonyl Compounds", *Tetrahedron 52 (10)*, 3547-3552 (1996).
Filling et al., "Critical Residues for Structure and Catalysis in Short-chain Dehydrogenases/Reductases", *J. Biol. Chem. 277*, 25677-25684 (2002).
Forrest et al., "Carbonyl reductase", *Chem. Biol. Interact. 129*, 21-40 (2000).
Gruber et al., "From a Racemate to a Single Enantiomer: Deracemization by Stereoinversion", *Adv. Synth. Catal. 348*, 1789-1805 (2006).
Higgins et al., "Fast and sensitive multiple sequence alignments on a microcomputer", *CABIOS Communications*, 5 (2), 151-153 (1989).
Huang et al., "Parallelization of a local similarity algorithm", *CABIOS*, 8 (2), 155-165 (1992).
Itoh et al., "Production of chiral alcohols by enantioselective reduction with NADH-dependent phenylacetaldehyde reductase from Corynebacterium straun, ST-10", *J. Mol. Catal. B. Enzym.* 6, 41-50 (1999).
Itsuno et al., "Asymmetric Synthesis Using Chirally Modified Borohydrides. Part 3. Enantioselective Reduction of Ketones and Oxime Ethers with Reagents Prepared from Borane and Chiral Amino Alcohols", *J. Chem. Soc. Perkin Trans. I*, 2039-2044 (1985).
Iwasaki et al., "Nonenzymatic Kinetic Resolution of 1,2-Diols Catalyzed by an Organotin Compound", *Org. Lett. 1 (7)*, 969-972 (1999).
Jones, "The first filamentous fungal genome sequences: Aspergillus leads the way for essential everyday resources or dusty museum specimens?", *Microbiology 153*, 1-6 (2007).

(Continued)

*Primary Examiner* — Tekchand Saidha
(74) *Attorney, Agent, or Firm* — Viksnins Harris & Padys PLLP

(57) ABSTRACT

Stereospecific carbonyl reductases SCR1, SCR2, and SCR3 are described herein as are nucleotide sequences that encode these reductases. These stereospecific carbonyl reductases have anti-Prelog selectivity and have specificities that are useful for fine biochemical synthesis.

24 Claims, 7 Drawing Sheets

(56) References Cited

OTHER PUBLICATIONS

Kallberg et al., "Short-chain dehydrogenases/reductases (SDRs) Coenzyme-based functional asignments in completed genomes", *Eur. J. Biochem.* 269, 4409-4417 (2002).
Kamble et al., "Biocatalytic synthesis of S(-)-1-(1'-naphthyl) ethanol by a novel isolate of *Candida viswanathii*", *J. Mol. Catal. B Enzym.* 35, 1-6 (2005).
Kamitori et al., "X-ray Structures of NADPH-dependent Carbonyl Reductase from Sporobolomyces salmaonicolor Provide Insights into Stereoselective Reductions of Carbonyl Compounds", *J. Mol. Biol.* 352, 551-558 (2005).
Karlin et al., "Methods for assessing the statistical significance of molecular sequence features by using general scoring schemes", *Proc. Natl. Acad. Sci. USA*, 87, 2264-2268 (1990).
Karlin et al., Applications and statistics for multiple high-scoring segments in molecular sequences, *Proc. Natl. Acad. Sci. USA*, 90, 5873-5877 (1993).
Kataoka et al., "Gene cloning and overexpression of two conjugated polyketone reductases, novel aldo-keto reductase family enzymes, of *Candida parapsilosis*", *Appl Microbiol Biotechnol* 64, 359-366 (2004).
Kataoka et al., "Gene cloning of an NADPH-dependent menadione reductase from Candida macedoniensis, and its application to chiral alcohol production", *Enzyme Microb. Technol.* 38, 944-951 (2006).
Katz et al., "Screening of two complementary collections of *Saccharomyces cerevisiae* to identify enzymes involved in stereo-selective reductions of specific carbonyl compounds: an alternative to protein purification", *Enzyme Microb. Technol.* 33, 163-172 (2003).
Kroutil et al., "Recent advances in the biocatalytic reduction of ketones and oxidation of sec-alcohols", *Curr. Opin. Chem. Biol.* 8, 120-126 (2004).
Liese et al., "Enzymatic Resolution of 1-Phenyl-1,2-ethanediol by Enantioselective Oxidation: Overcoming Product Inhibition by Continuous Extraction", *Biotechnol. Bioeng.* 51, 544-550 (1996).
Manzocchi et al., "Stereochemical Control of Bakers' Yeast Mediated Reduction of a Protected 2-Hydroxy Ketone", *J. Org. Chem.* 53, 4405-4407 (1988).
Myers et al., "Optimal alignments in linear space", *CABIOS*, 4 (1), 11-17 (1988).
Needleman et al., "A General Method Applicable to the Search for Similarities in the Amino Acid Sequence of Two Proteins", *JMB*, 48, 443-453 (1970).
Nie et al., "Highly Enantioselective Conversion of Racemic 1-Phenyl-1,2-ethanediol by Stereoinversion Involving a Novel Cofactor-Dependent Oxidoreduction System of Candida parapsilosis CCTCC M203011", *Org. Process Res. Dev.* 8, 246-251 (2004).
Nie et al., "High-yield conversion of (R)-2-octanol from the corresponding racemate by stereoinversion using Candida rugosa", *Biotechnol. Lett.* 27, 23-26 (2005).
Nie et al., "Purification, Characterization, Gene Cloning, and Expression of a Novel Alcohol Dehydrogenase with Anti-Prelog Stereospecificity from Candida parapsilosis", *Appl. Environ. Microbiol.* 73(11), 3759-3764 (2007).
Nie et al., "A novel NADH-dependent carbonyl reductase with unusual stereoselectivity for (R)-specific reduction from an (S)-1-phenyl-1, 2-ethanediol-producing micro-organixm; purification and characterization", *Letters in Applied Microbiology*, vol. 44 (5), 555-562 (2007).
Niefind et al., "The Crystal Structure of R-specific Alcohol Dehydrogenase from *Lactobacillus brevis* Suggests the Structural Basis of its Metal dependency", *J. Mol. Biol.* 327, 317-328 (2003).

Oppermann et al., "Short-chain dehydrogenases/reductases (SDR) the 2002 update", *Chem. Biol. Interact. 143-144*, 247-253 (2003).
Panke et al., "Trends and innovations in industrial biocatalysis for the prosecution of fine chemicals", *Curr. Opin. Biotechnol.* 15, 272-279 (2004).
Patent Cooperation Treaty, International Searching Authority, Search Report and Written Opinion for PCT/US2010/039666, 21 pages, Sep. 2, 2010.
Pearson et al., "Improved tools for biological sequence comparison", *Proc. Natl. Acad. Sci. USA*, 85, 2444-2448 (1988).
Pearson et al., "Using the FASTA Program to Search Protein and DNA Sequence Databases", *Meth. Mol. Biol.*, 24, 307-331 (1994).
Pollard et al., "Asymmetric Reduction of α, β-Unsaturated Ketone to ® Allylic Alcohol by *Candida chilensis*", *Biotechnol. Bioeng.* 93, 674-686 (2006).
Prelog, "Specification of the Stereospecificity of Some Oxido-Reductases by Diamond Lattice Sections", *Pure Appl.Chem.* 9, 119-130 (1964).
Raskin et al. "Bacterial Genomics and Pathogen Evolution", *Cell* 124, 703-714 (2006).
Reid et al., "Molecular Characterization of Microbial Alcohol Dehydrogenases", *Critical Reviews in Microbiology* 20 (1), 13-56 (1994).
Schmid et al., "Industrial biocatalysis today and tomorrow", *Nature* 409, 258-268 (2001).
Schoemaker et al., "Dispelling the Myths—Biocatalysis in Industrial Synthesis", *Science* 299, 1694-1697 (2003).
Secundo et al., "Effects of pH on enantiospecificity of alcohol dehydrogenases from Thermoanaerobacter ethanolicus and horse liver", *Enzyme Microb. Technol.* 19, 487-792 (1996).
Smith et al., "Comparison of Biosequences", *Adv. Appl. Math.*, 2, 482-489 (1981).
Voss et al., "Deracemization of Secondary Alcohols through a Concurrent Tandem Biocatalytic Oxidation and Reduction", *Angew. Chem. Int. Ed.* 47, 741-745 (2008).
Voss et al., "Orchestration of Concurrent Oxidation Stereoinversion and Deracemisation of sec-Alcohols", *J. Am. Chem. Soc. 130*, 13969-13972 (2008).
Wei et al., "Microbial Transformation of 2-Hydroxy and 2-Acetoxy Ketones with Geotrichum sp.", *Bioorg. Med. Chem.* 8, 1129-1137 (2000).
Wsol et al., "Sex Differences in Stereospecificity of Oracin Reductases in Rat In Vitro and In Vivo", *Chirality* 11, 505-509 (1999).
Yasohara et al., "Molecular Cloning and Overexpression of the Gene Encoding an NADPH-Dependent Carbonyl Reductase from Candida magnolia, Involved in Stereoselective Reduction of Ethyl 4-Chloro-3-oxobutanoate", *Biosci. Biotechnol. Biochem.*, 64 (7), 1430-1436 (2000).
Zhang et al., "Ser67Asp and His68Asp Substitutions in *Candida parapsilosis* Carbonyl Reductase Alter the Coenzyme Specificity and Enanioselectivity of Ketone Reduction", *Applied and Environmental Microbiology*, vol. 75 (7), 2176-2183 (2009).
Zhu et al., "Stereoselective Enzymatic Synthesis of Chiral Alcohols with the Use of a Carbonyl Reductase from *Candida* magnolia with Anti-Prelog Enantioselectivity", *J. Org. Chem.*, 71, 4202-4205 (2006).
Zhu et al., "A recombinant ketoreductase tool-box. Assessing the substrate selectivity and stereoselectivity toward the reduction of βketoesters", *Tetrahedron* 62, 901-905 (2006).

* cited by examiner

SEQUENCE LISTING

```
<160> NUMBER OF SEQ ID NOS: 12

<210> SEQ ID NO 1
<211> LENGTH: 279
<212> TYPE: PRT
<213> ORGANISM: Candida parapsilosis

<400> SEQUENCE: 1

Met Gly Glu Ile Glu Ser Tyr Cys Asn Lys Glu Leu Gly Pro Leu Pro
1               5                   10                  15

Thr Lys Ala Pro Thr Leu Ser Lys Asn Val Leu Asp Leu Phe Ser Leu
            20                  25                  30

Lys Gly Lys Val Ala Ser Val Thr Gly Ser Ser Gly Gly Ile Gly Trp
        35                  40                  45

Ala Val Ala Glu Ala Tyr Ala Gln Ala Gly Ala Asp Val Ala Ile Trp
    50                  55                  60

Tyr Asn Ser His Pro Ala Asp Glu Lys Ala Glu His Leu Gln Lys Thr
65                  70                  75                  80

Tyr Gly Val His Ser Lys Ala Tyr Lys Cys Asn Ile Ser Asp Pro Lys
                85                  90                  95

Ser Val Glu Glu Thr Ile Ser Gln Gln Glu Lys Asp Phe Gly Thr Ile
            100                 105                 110

Asp Val Phe Val Ala Asn Ala Gly Val Thr Trp Thr Gln Gly Pro Glu
        115                 120                 125

Ile Asp Val Asp Asn Tyr Asp Ser Trp Asn Lys Ile Ile Ser Val Asp
    130                 135                 140

Leu Asn Gly Val Tyr Tyr Cys Ser His Asn Ile Gly Lys Ile Phe Lys
145                 150                 155                 160

Lys Asn Gly Lys Gly Ser Leu Ile Ile Thr Ser Ser Ile Ser Gly Lys
                165                 170                 175
```

```
Ile Val Asn Ile Pro Gln Leu Gln Ala Pro Tyr Asn Thr Ala Lys Ala
            180                 185                 190

Ala Cys Thr His Leu Ala Lys Ser Leu Ala Ile Glu Trp Ala Pro Phe
        195                 200                 205

Ala Arg Val Asn Thr Ile Ser Pro Gly Tyr Ile Asp Thr Asp Ile Thr
    210                 215                 220

Asp Phe Ala Ser Lys Asp Met Lys Ala Lys Trp Trp Gln Leu Thr Pro
225                 230                 235                 240

Leu Gly Arg Glu Gly Leu Thr Gln Glu Leu Val Gly Gly Tyr Leu Tyr
                245                 250                 255

Leu Ala Ser Asn Ala Ser Thr Phe Thr Thr Gly Ser Asp Val Val Ile
            260                 265                 270

Asp Gly Gly Tyr Thr Cys Pro
            275

<210> SEQ ID NO 2
<211> LENGTH: 279
<212> TYPE: PRT
<213> ORGANISM: Candida parapsilosis

<400> SEQUENCE: 2

Met Gly Glu Ile Glu Ser Tyr Cys Asn Lys Glu Leu Gly Pro Leu Pro
1               5                   10                  15

Thr Lys Ala Pro Thr Leu Ala Lys Asn Val Leu Asp Leu Phe Ser Leu
            20                  25                  30

Lys Gly Lys Val Ala Ser Val Thr Gly Ser Ser Gly Gly Ile Gly Trp
        35                  40                  45

Ala Val Ala Glu Ala Tyr Ala Gln Ala Gly Ala Asp Val Ala Ile Trp
    50                  55                  60

Tyr Asn Ser His Pro Ala Asp Glu Lys Ala Glu His Leu Gln Lys Thr
65                  70                  75                  80

Tyr Gly Val Arg Ser Lys Ala Tyr Lys Cys Asn Ile Ser Asp Pro Lys
                85                  90                  95

Ser Val Glu Glu Thr Ile Ser Gln Gln Glu Lys Asp Phe Gly Thr Ile
            100                 105                 110

Asp Val Phe Val Ala Asn Ala Gly Ile Pro Trp Ala Asp Gly Pro Val
        115                 120                 125

Ile Asp Leu Glu Asn Tyr Asp Ala Trp Asn Lys Leu Ile Asn Thr Asp
    130                 135                 140

Ile Asn Gly Val Phe Tyr Cys Ala His Ser Ile Gly Lys Ile Phe Lys
145                 150                 155                 160

Lys Asn Gly Lys Gly Ser Leu Ile Ile Thr Ala Ser Leu Ala Gly Ser
                165                 170                 175

Val Val Thr Ile Pro Gln Gln Gln Thr Pro Tyr Asn Thr Ala Lys Ala
            180                 185                 190

Ala Cys Leu His Leu Ala Lys Ser Leu Ala Val Glu Trp Ala Pro Phe
        195                 200                 205

Ala Arg Val Asn Thr Val Ser Pro Gly Tyr Phe Glu Thr Glu Ile Asn
    210                 215                 220

Gly Phe Ala Asp Glu Asp Met Arg Glu Lys Trp Tyr Gln Leu Thr Pro
225                 230                 235                 240

Leu Gly Arg Met Gly Ile Thr Glu Glu Leu Val Gly Gly Tyr Leu Tyr
                245                 250                 255

Phe Ala Ser Asn Ala Ser Thr Phe Thr Thr Gly Ser Asp Leu Ile Ile
            260                 265                 270
```

```
Asp Gly Gly Phe Thr Cys Pro
        275

<210> SEQ ID NO 3
<211> LENGTH: 279
<212> TYPE: PRT
<213> ORGANISM: Candida parapsilosis

<400> SEQUENCE: 3

Met Gly Glu Ile Glu Ser Tyr Cys Asn Lys Glu Leu Gly Pro Leu Pro
1               5                   10                  15

Thr Lys Ala Pro Thr Leu Ser Lys Asn Val Leu Asp Leu Phe Ser Leu
            20                  25                  30

Lys Gly Lys Val Ala Ser Val Thr Gly Ser Ser Gly Gly Ile Gly Trp
        35                  40                  45

Ala Val Ala Glu Ala Tyr Ala Gln Ala Gly Ala Asp Val Ala Ile Trp
    50                  55                  60

Tyr Asn Ser His Pro Ala Asp Glu Lys Ala Glu His Leu Gln Lys Thr
65                  70                  75                  80

Tyr Gly Val Arg Ser Lys Ala Tyr Lys Cys Asn Ile Ser Asp Pro Lys
                85                  90                  95

Ser Val Glu Glu Thr Ile Ser Gln Gln Glu Lys Asp Phe Gly Thr Ile
            100                 105                 110

Asp Val Phe Val Ala Asn Ala Gly Val Pro Trp Thr Glu Gly Pro Glu
        115                 120                 125

Ile Asn Val Asp Asn Tyr Asp Ser Trp Asn Lys Ile Ile Asn Leu Asp
    130                 135                 140

Leu Asn Gly Val Tyr Tyr Cys Ala His Thr Val Gly Lys Ile Phe Lys
145                 150                 155                 160

Lys Asn Gly Lys Gly Ser Leu Val Ile Thr Ser Ser Met Ser Gly Thr
                165                 170                 175

Ile Val Asn Val Pro Gln Leu Gln Ala Ala Tyr Asn Ala Ala Lys Ala
            180                 185                 190

Ala Cys Thr His Leu Thr Lys Ser Leu Ala Val Glu Trp Ala Pro Phe
        195                 200                 205

Ala Arg Val Asn Cys Val Ser Pro Gly Tyr Ile Ala Thr Glu Ile Ser
    210                 215                 220

Asp Phe Val Glu Lys Asp Met Lys Ala Lys Trp Trp Gln Leu Thr Pro
225                 230                 235                 240

Leu Gly Arg Glu Gly Leu Ala Gln Glu Leu Val Gly Ala Tyr Leu Tyr
                245                 250                 255

Leu Ala Ser Asn Ala Ser Thr Tyr Thr Thr Gly Ala Asn Leu Ala Val
            260                 265                 270

Asp Gly Gly Tyr Thr Cys Pro
        275

<210> SEQ ID NO 4
<211> LENGTH: 281
<212> TYPE: PRT
<213> ORGANISM: Candida parapsilosis

<400> SEQUENCE: 4

Met Ser Lys Asp Glu Thr Ile Ser Tyr Cys Asn Asp Gln Leu Gly Pro
1               5                   10                  15

Leu Pro Thr Thr Ala Pro Lys Val Ser Asp Asn Val Thr Asp Leu Phe
            20                  25                  30
```

Ser Phe Lys Gly Lys Val Val Ser Val Thr Gly Ser Ser Gly Gly Ile
    35                  40                  45

Gly Trp Ala Val Ala Glu Gly Phe Ala Gln Ala Gly Ala Asp Val Ala
    50                  55                  60

Ile Trp Tyr His Ser His Asn Ala Asp Glu Lys Ala Lys Tyr Leu Gln
65                  70                  75                  80

Glu Lys Tyr Gly Val Lys Ser Ile Ala Tyr Gly Cys Asn Ile Gly Val
                85                  90                  95

Ala Glu Glu Val Gln Lys Thr Val Asp Gln Ile Glu Ser Asp Phe Gly
                100                 105                 110

Lys Ile Asp Val Phe Val Ala Asn Ala Gly Ile Pro Trp Thr Asp Gly
            115                 120                 125

Pro Glu Ile Asp Val Gln Asp Leu Ser Lys Trp Thr Lys Ile Ile Asp
        130                 135                 140

Thr Asp Leu Asn Ser Val Tyr Tyr Cys Ala His Ala Ile Gly Pro Ile
145                 150                 155                 160

Phe Arg Lys Gln Gly Lys Gly Ser Leu Val Ile Thr Ala Ser Met Ser
                165                 170                 175

Ala Thr Ile Val Asn Val Pro Gln Leu Gln Ala Ala Tyr Asn Val Ala
                180                 185                 190

Lys Ala Gly Val Lys His Leu Ser Lys Ser Leu Ala Val Glu Trp Ala
            195                 200                 205

Pro Phe Ala Arg Val Asn Ser Val Ser Pro Gly Tyr Ile Ser Thr Asn
        210                 215                 220

Leu Thr Thr Phe Ala Asn Pro Asp Leu Gln Lys Lys Trp Val Gln Leu
225                 230                 235                 240

Thr Pro Leu Gly Arg Glu Gly His Pro Lys Glu Leu Val Gly Ala Tyr
                245                 250                 255

Leu Tyr Leu Ala Ser Asp Ala Ala Thr Phe Thr Thr Gly Cys Asp Leu
                260                 265                 270

Ala Val Asp Gly Gly Tyr Thr Val Pro
            275                 280

<210> SEQ ID NO 5
<211> LENGTH: 837
<212> TYPE: DNA
<213> ORGANISM: Candida parapsilosis

<400> SEQUENCE: 5
atgggcgaaa tcgaatctta ttgtaacaaa gagttgggac cattgccaac aaaagctcca      60
actttgtcaa agaacgtgct tgacttgttt tcccttaagg gtaaagttgc ttctgtgact     120
ggatcatctg gtggtattgg ttgggctgtt gctgaagctt acgctcaagc tggtgcagat     180
gtagccattt ggtacaactc ccatccagct gatgagaaag ccgaacactt gcaaagaca     240 tatggggtcc attcgaaagc ttacaagtgt aacattagtg acccaaagag cgttgaagaa     300
accatctctc aacaagaaaa agactttgga accatcgacg tgtttgtcgc taatgctggt     360
gttacttgga cacaaggacc agagattgat gttgacaact acgattcatg aataagata     420 attagtgttg atttgaatgg cgtatactac tgctcacaca atatcggtaa gatcttcaaa     480
aaaaacggca aagggtcttt gatcataaca tcatcgatat ccggcaagat tgtcaatatc     540
cctcagcttc aagctccata taacacggct aaagctgctt gtacacattt ggcaaaatcc     600
ttggccatcg agtgggcacc atttgctaga gtgaacacca tttcaccagg ttatattgat     660
actgatatta cagattttgc aagcaaagat atgaaagcta agtggtggca attgacacca      720
ttgggaaggg aggggcttac tcaagagcta gttggtggat atttgtactt ggcatcgaat      780
gcgtctacat tcacaactgg ttctgatgtt gttattgacg gtggatacac gtgtcca        837

<210> SEQ ID NO 6
<211> LENGTH: 837
<212> TYPE: DNA
<213> ORGANISM: Candida parapsilosis

<400> SEQUENCE: 6
atgggcgaaa tcgaatctta ttgtaacaaa gagttgggac cattgccaac aaaagctcca       60
actttggcaa agaacgtgct tgacttgttt tcccttaagg gtaaagttgc ttctgtgact      120
ggatcatctg gtggtattgg ttgggctgtt gctgaggctt acgctcaagc tggtgcagat      180
gtagccattt ggtacaactc ccatccagct gatgagaaag ccgaacactt gcaaaagaca      240
tatggggtcc gttcgaaagc ttacaagtgt aacattagtg acccaaagag cgttgaagaa      300
accatctctc aacaagaaaa agactttgga accattgacg tgtttgtcgc taatgctggt      360
attccttggg ctgatggtcc ggtgattgac cttgaaaaact acgatgcatg gaataaactc      420
atcaacaccg acatcaatgg tgtgttttac tgcgcacaca gtatcggtaa gatcttcaaa      480
aagaatggaa aggatccctt aattattact gcttcactcg ctggttctgt tgtcactatt      540
ccgcaacaac aaactcctta taatactgcg aaagccgctt gtcttcattt ggcaaaatca      600
ttggcggttg agtgggcgcc atttgctaga gtcaataccg tttcaccagg ctactttgaa      660
accgagatca atggattcgc agacgaggat atgcgtgaaa agtggtatca attgacgcca      720 tgggaagaa tggaataac tgaagagcta gttggtgggt atttgtactt tgcttctaat       780
gcatctacat tcacaacagg ctctgatctt attatcgatg gtggattcac ctgtcca        837

<210> SEQ ID NO 7
<211> LENGTH: 837
<212> TYPE: DNA
<213> ORGANISM: Candida parapsilosis

<400> SEQUENCE: 7
atgggcgaaa tcgaatctta ttgcaacaaa gagttgggac cattgccaac aaaagctcca       60
actttgtcaa agaacgtgct tgacttgttt tcccttaagg gtaaagttgc ttctgtgact      120
ggatcatctg gtggtattgg ttgggctgtt gctgaggctt acgctcaagc tggtgcagac      180
gtagccattt ggtacaactc ccatccagct gatgagaaag ctgaacactt gcaaaagaca      240
tatggggtcc gttcgaaagc ttacaagtgt aacattagtg acccaaagag cgttgaagaa      300
accatctctc aacaagaaaa agactttgga accattgacg tgtttgtcgc taatgctggt      360
gtgccttgga ctgaaggacc tgaaatcaat gtcgataact acgattcatg gaacaaaatt      420
atcaacctag acttgaatgg tgtatactac tgtgctcata ccgttggtaa gattttcaag      480
aaaaacggca aaggctcctt ggtgattact tcatccatgt cgggtaccat tgttaatgtt      540
cctcaattgc aagcagccta caatgcagca aaagctgctt gcactcattt gactaaatcc      600
ttagcagttg aatgggctcc atttgctaga gtgaattgtg tttctccagg ttacattgcc      660
actgaaattt ctgattttgt tgaaaaagac atgaaagcca agtggtggca attgacacca      720 tgggaaggg aaggttttggc ccaagaattg gttggtgctt acttgtattt ggcatctaat      780
gcttcgactt atactactgg tgctaaccte gctgtcgatg gtggttacac ttgtcca        837

```
<210> SEQ ID NO 8
<211> LENGTH: 843
<212> TYPE: DNA
<213> ORGANISM: Candida parapsilosis

<400> SEQUENCE: 8
atgagtaaag acgaaacaat ttcttactgt aatgaccaat tgggcccatt gccaaccaca      60
gctccaaaag tatctgataa cgttactgac cttttctcct tcaaaggtaa agttgtgtca     120
gtaaccgggt cctccggagg tattggttgg gctgttgctg agggcttcgc tcaagctggt     180
gcagatgtag ccatttggta tcattctcac aatgctgatg aaaaggccaa atatctccaa     240
gaaaaatacg gagtcaagtc aattgcttat ggatgtaaca ttggtgttgc tgaggaagtc     300
caaaaaacag ttgatcaaat tgaatctgat ttcggtaaga ttgacgtttt cgttgccaac     360
gctggtattc catggacgga tggaccagaa attgatgttc aagatttaag caaatggacc     420
aagattatcg acactgattt gaacagtgta tattactgtg ctcatgccat tggtcctatt     480
ttcagaaaac aaggtaaagg ctcattggtt attactgcat ccatgtcggc tacaattgtc     540
aatgttccgc aattgcaagc agcttataat gttgccaaag ctggggttaa gcacttgtca     600
aagtcgttgg cggttgaatg ggctcctttt gccagagtca acagtgtctc accaggttat     660
atttcaacaa atttgacaac ctttgccaac cctgatttgc aaaagaaatg ggtgcaattg     720
actccattgg gtagagaagg gcatccaaag gaattggttg gtgcttactt atacttggct     780
tccgatgctg ctactttcac aactggttgt gatttagctg ttgatggtgg ttatactgtc     840
cca                                                                  843

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      Cofactor-binding motif peptide
<220> FEATURE:
<221> NAME/KEY: MOD_RES
<222> LOCATION: (2)..(4)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 9

Gly Xaa Xaa Xaa Gly Xaa Gly
1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      catalytic tetrad peptide

<400> SEQUENCE: 10

Asn Ser Tyr Lys
1

<210> SEQ ID NO 11
<211> LENGTH: 3
<212> TYPE: PRT
<213> ORGANISM: Artificial Sequence
<220> FEATURE:
```

-continued

```
<223> OTHER INFORMATION: Description of Artificial Sequence: Synthetic
      catalytic triad peptide

<400> SEQUENCE: 11

Ser Tyr Lys
1

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 12

His His His His His His
1               5
```

STEREOSPECIFIC CARBONYL REDUCTASES

CROSS-REFERENCE TO RELATED APPLICATION(S)

This application is a divisional of U.S. application Ser. No. 13/379,942, filed Jul. 10, 2012, now abandoned, which is a 35 U.S.C. §371 application of International Application No. PCT/US2010/039666, filed Jun. 23, 2010, which claims the benefit of U.S. Provisional Application Ser. No. 61/219,610, filed Jun. 23, 2009, now expired. The entire content of the applications referenced above are hereby incorporated by reference herein.

STATEMENT OF GOVERNMENT SUPPORT

This invention was made with government support under U54 GM074958 awarded by the National Institutes of General Medical Science, Protein Structure Initiative program. The government has certain rights in the invention.

SEQUENCE LISTING

The instant application contains a Sequence Listing which has been submitted electronically in ASCII format and is hereby incorporated by reference in its entirety. Said ASCII copy is named 08035.030US1_SL.txt and is 15,864 bytes in size.

BACKGROUND

The NAD(P)H-dependent carbonyl reductases catalyze reduction of a variety of endogenous and xenobiotic carbonyl compounds, including biologically and pharmacologically active substrates (Forrest et al., Chem. Biol. Interact., 129, 21-40 (2000)). There is considerable interest in the use of carbonyl reductases in the pharmaceutical and fine chemicals industries for the production of chiral alcohols, which are important building blocks for the synthesis of chirally-pure compounds, e.g., pharmaceutical agents (Panke et al., Curr. Opin. Biotechnol., 15, 272-279 (2004); Schmid et al., Nature, 409, 258-268 (2001); and Schoemaker et al., Science, 299, 1694-1697 (2003)). For such chiral auxiliaries, production from their corresponding prochiral ketones, the use of carbonyl reductases has advantages over chemo-catalysts in terms of their highly chemo-, enantio-, and regioselectivities. These features make stereospecific carbonyl reductases very useful from both scientific and industrial perspectives (Kroutil et al., Curr. Opin. Chem. Biol., 8, 120-126 (2004)). However, the range of current applications for stereospecific carbonyl reductases remains modest. This can be attributed to several limitations, including the stereospecificity and availability of enzymes. In addition, research on molecular mechanisms of oxidoreductases is still in its infancy. Further, most enzymes that can catalyze asymmetric reductions generally follow Prelog's rule in terms of stereochemical outcomes (Bradshaw et al., J. Org. Chem., 57, 1526-1532 (1992); Ernst et al., Appl. Microbiol. Biotechnol., 66, 629-634 (2005); Niefind et al., J. Mol. Biol., 327, 317-328 (2003); Prelog, Pure Appl. Chem., 9, 119-130 (1964)). Enzymes with anti-Prelog stereospecificity are quite rare, and only few have been isolated and characterized in purified forms (De Wildeman et al., Acc. Chem. Res. 40, 1260-1266, (2007)). Accordingly, stereospecific carbonyl reductases are needed. In particular, stereospecific carbonyl reductases with anti-Prelog stereospecificity are needed.

SUMMARY OF CERTAIN EMBODIMENTS OF THE INVENTION

Accordingly, as described herein, three stereospecific carbonyl reductase genes (scr1, scr2, and scr3) from C. parapsilosis have been discovered. These genes have been cloned and expressed, and the encoded proteins purified to homogeneity and confirmed to function as stereospecific carbonyl reductases (SCR1, SCR2, and SCR3). These stereospecific carbonyl reductases have anti-Prelog selectivity and convert 2-hydroxyacetophenone to (S)-1-phenyl-1,2-ethanediol (PED). These oxidoreductases have useful specificities that are useful for fine biochemical synthesis.

Application of biocatalysis in the synthesis of chiral molecules is one of the greenest technologies for the replacement of chemical routes. This is due to environmentally benign reaction conditions for biocatalysis and unparalleled chemo-, regio- and stereoselectivities. The newly identified stereospecific carbonyl reductases (SCRs) showed high catalytic activities for producing (S)-1-phenyl-1,2-ethanediol (PED) from 2-hydroxyacetophenone with NADPH as the coenzyme. The enzymes from this cluster are carbonyl reductases with novel anti-Prelog stereoselectivity. Of the enzymes encoded in the gene cluster, SCR1 and SCR3 exhibited distinct specificities to acetophenone derivatives and chloro-substituted 2-hydroxyacetophenones, and especially very high activities to ethyl 4-chloro-3-oxobutyrate, which affords ethyl 4-chloro-3-hydroxybutyrate, a precursor of the chiral side chain in the synthesis of atorvastatin (Lipitor®) and rosuvastatin, e.g., rosuvastatin calcium (Crestor®).

DETAILED DESCRIPTION

Figure 1:
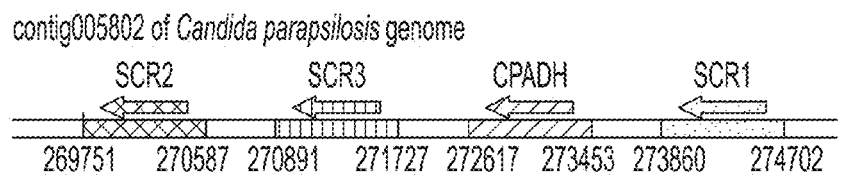
FIG. 1. Map of contig005802 of Candida parapsilosis genome including the four open reading frames, scr1, scr2, scr3, and cpadh.

Certain embodiments of the present invention provide a purified polypeptide, the sequence of which comprises an amino acid sequence that has at least 70% identity to a *Candida parapsilosis* stereospecific carbonyl reductase, wherein the polypeptide has carbonyl reductase activity and does not comprise SEQ ID NO:1.

In certain embodiments, the amino acid sequence has at least 70% identity to at least one of the *Candida parapsilosis* stereospecific carbonyl reductases represented by SEQ ID NO:2, SEQ ID NO:3 or SEQ ID NO:4.

In certain embodiments, the amino acid sequence has at least 70% identity to SEQ ID NO:2.

In certain embodiments, the amino acid sequence has at least 70% identity to SEQ ID NO:3.

In certain embodiments, the amino acid sequence has at least 70% identity to SEQ ID NO:4.

In certain embodiments, the amino acid sequence has at least 75% identity to the *Candida parapsilosis* stereospecific carbonyl reductase (e.g., to at least one of SEQ ID NO:2, SEQ ID NO:3 or SEQ ID NO:4).

In certain embodiments, the amino acid sequence has at least 80% identity to the *Candida parapsilosis* stereospecific carbonyl reductase (e.g., to at least one of SEQ ID NO:2, SEQ ID NO:3 or SEQ ID NO:4).

In certain embodiments, the amino acid sequence has at least 85% identity to the *Candida parapsilosis* stereospecific carbonyl reductase (e.g., to at least one of SEQ ID NO:2, SEQ ID NO:3 or SEQ ID NO:4).

In certain embodiments, the amino acid sequence has at least 90% identity to the *Candida parapsilosis* stereospecific carbonyl reductase (e.g., to at least one of SEQ ID NO:2, SEQ ID NO:3 or SEQ ID NO:4).

In certain embodiments, the amino acid sequence has at least 95% identity to the *Candida parapsilosis* stereospecific carbonyl reductase (e.g., to at least one of SEQ ID NO:2, SEQ ID NO:3 or SEQ ID NO:4).

In certain embodiments, the amino acid sequence has at least 99% identity to the *Candida parapsilosis* stereospecific carbonyl reductase (e.g., to at least one of SEQ ID NO:2, SEQ ID NO:3 or SEQ ID NO:4).

In certain embodiments, the amino acid sequence comprises SEQ ID NO:9, SEQ ID NO:10 or SEQ ID NO:11.

In certain embodiments, the amino acid sequence comprises SEQ ID NO:9, SEQ ID NO:10 and SEQ ID NO:11.

In certain embodiments, the amino acid sequence comprises SEQ ID NO:2.

In certain embodiments, the amino acid sequence comprises SEQ ID NO:3.

In certain embodiments, the amino acid sequence comprises SEQ ID NO:4.

In certain embodiments, the sequence of the polypeptide consists essentially of, or consists of, SEQ ID NO:2, SEQ ID NO:3 or SEQ ID NO:4.

In certain embodiments, the carbonyl reductase activity of the polypeptide is NADPH-dependent.

In certain embodiments, the polypeptide is an anti-Prelog-type stereospecific carbonyl reductase.

Certain embodiments of the present invention provide composition comprising the polypeptide as described herein.

Certain embodiments of the present invention provide an isolated nucleic acid sequence comprising a sequence that encodes a polypeptide described herein.

In certain embodiments, the sequence comprises SEQ ID NO:6 or of a degenerate variant of SEQ ID NO:6.

In certain embodiments, the sequence comprises SEQ ID NO:7 or of a degenerate variant of SEQ ID NO:7.

In certain embodiments, the sequence comprises SEQ ID NO:8 or of a degenerate variant of SEQ ID NO:8.

In certain embodiments, the sequence encodes SEQ ID NO:2.

In certain embodiments, the sequence encodes SEQ ID NO:3.

In certain embodiments, the sequence encodes SEQ ID NO:4.

Certain embodiments of the present invention provide an expression vector comprising an expression cassette operably linked to a nucleic acid molecule as described herein.

Certain embodiments of the present invention provide a host cell comprising a vector as described herein.

Certain embodiments of the present invention provide a method of reducing a carbonyl substrate, comprising contacting the substrate with a polypeptide described herein, or a composition described herein, in conditions suitable to catalyze the reduction of the carbonyl substrate. As used herein, a "carbonyl substrate" is a substrate that comprises at least one carbonyl group, such as a compound that comprises an α-ketoester, a β-ketoester, an aryl ketone or an aliphatic ketone (see, e.g., FIG. 7). The polypeptide having carbonyl reductase activity reduces a carbonyl group of the carbonyl substrate.

In certain embodiments, the reduction takes place in the presence of a coenzyme.

In certain embodiments, the coenzyme is NADPH.

In certain embodiments, the carbonyl substrate comprises an α-ketoester, a β-ketoester, an aryl ketone or an aliphatic ketone.

In certain embodiments, the carbonyl substrate comprises an α-ketoester.

In certain embodiments, the α-ketoester is methyl pyruvate, methyl phenylglyoxylate, ethyl pyruvate or ethyl benzoylformate.

In certain embodiments, the carbonyl substrate comprises a β-ketoester.

In certain embodiments, the β-ketoester is ethyl trifluoroacetoacetate, methyl acetoacetate, methyl 3-oxovalerate, methyl 4-fluorobenzoylacetate, ethyl acetoacetate, ethyl 3-oxovalerate, ethyl 4-chloroacetoacetate, ethyl benzoylacetate, or ethyl 3,4-dimethoxybenzoylacetate.

In certain embodiments, the carbonyl substrate comprises an aryl ketone.

In certain embodiments, the aryl ketone is 2-hydroxyacetophenone, or a derivative thereof.

In certain embodiments, the aryl ketone is 2'-chloro-2-hydroxyacetophenone, 3'-chloro-2-hydroxyacetophenone, 4'-chloro-2-hydroxyacetophenone or 4'-methoxy-2-hydroxyacetophenone.

In certain embodiments, the carbonyl substrate comprises an aliphatic ketone.

In certain embodiments, the aliphatic ketone is 2-butanone, 2-pentanone, 2-hexanone, 2-heptanone, 2-octanone or 2-methyl-3-pentanone In certain embodiments, the carbonyl substrate is ethyl 4-chloro-3-oxobutyrate.

In certain embodiments, the reduction takes place at pH ranging from 5.0 to 6.0 (e.g., at about 5.0, 5.5 or 6.0).

Described herein is a new gene cluster of enantioselective oxidoreductases with unusual stereospecificity in C. parapsilosis. It was confirmed that these genes code for three unique stereospecific carbonyl reductases through cloning, expression, and purification of the corresponding gene products, and verification of enantiomer configuration of the enzymatic products of asymmetric reduction of prochiral carbonyl groups of multiple substrates. SCR1, SCR2, and SCR3 all exhibit a novel anti-Prelog stereospecificity in reducing prochiral carbonyl groups; e.g., forming (S)-1-phenyl-1,2-ethanediol from the corresponding ketone substrate, 2-hydroxyacetophenone. The enzymes are, however, distinct in their catalytic properties, including their pH dependency and substrate specificity spectrum.

According to catalytic properties and primary structure information, stereospecific oxidoreductases, including alcohol dehydrogenases and carbonyl reductases, are mainly classified into three different groups, the zinc-dependent alcohol dehydrogenase, the short-chain dehydrogenase/reductase (SDR), and the aldo-keto reductase (AKR) (Kamitori et al., J. Mol. Biol., 352, 551-558 (2005); Reid and Fewson, Crit. Rev. Microbiol., 20, 13-56 (1994)). These proteins share sequence motifs characteristic of the SDR superfamily, including the cofactor-binding motif Gly-X-X-X-Gly-X-Gly (X denotes any amino acid; SEQ ID NO:9), the catalytic triad of Ser-Tyr-Lys (SEQ ID NO:11), and also the extended tetrad of Asn-Ser-Tyr-Lys (SEQ ID NO:10) observed in the majority of SDRs (Filling et al., J. Biol. Chem. 277, 25677-25684 (2002)). In addition, the SCRs also have the conserved sequence motifs of secondary structural elements and key positions for assignment of coenzyme specificity of the cP2 subfamily in classic SDRs, except that the conserved basic residue K/R responsible for binding phosphate group in NADPH is replaced by weak basic residue H (Kallberg et al., Eur. J. Biochem., 269, 4409-4417 (2002)). These highly-conserved, characteristic sequence motifs indicate that the SCRs belong to the cP2 subfamily of the classical SDR superfamily, one of the three NADPH-dependent subfamilies (Kallberg et al., Eur. J. Biochem., 269, 4409-4417 (2002)).

Oxidoreductases perform a wide variety of asymmetric reductions, differing in stereospecificity and substrate specificity, and have been used for producing optically active alcohols from various prochiral ketones, ketoacids, and ketoesters. The SCRs catalyze (S)-specific reduction of 2-hydroxyacetophenone, an anti-Prelog type reaction (Manzocchi et al., J. Org. Chem., 53, 4405-4407, (1988); Prelog, Pure Appl. Chem., 9, 119-130 (1964)). Therefore, these new enzymes complement the stereospecific oxidoreductases described to date for catalysis of the reduction of prochiral carbonyl compounds to the corresponding optically pure alcohols with anti-Prelog stereopreference. Additionally, the finding of stereospecific carbonyl reductases from the same host provides profound knowledge on the reaction mechanism of C. parapsilosis whole-cell mediated stereoinversion, involving the oxidation step of (R)-PED to the intermediate (2-hydroxyacetophenone) and the reduction step of the intermediate to (S)-PED (Gruber et al., Adv. Synth. Catal., 348, 1789-1805 (2006); Nie et al., Org. Process Res. Dev., 8, 246-251 (2004); Nie et al., Appl. Environ. Microbiol., 73, 3759-3764 (2007); Voss et al., Angew. Chem. Int. Ed., 47, 741-745 (2008); Voss et al., J. Am. Chem. Soc., 130, 13969-13972 (2008)). It is worthy to note that SCR1 catalyzes the reduction of a broad spectrum of ketones including aryl, aliphatic ketones, α- and β-ketoesters, and shows a particular highest substrate specificity towards ethyl 4-chloro-3-oxobutyrate, a precursor for the synthesis of an important pharmaceutical intermediate. Therefore, the new discovered stereospecific carbonyl reductases will be useful enzymes with application potential.

The discovery of novel stereospecific carbonyl reductases of anti-Prelog selectivity further demonstrates the diversity of stereospecific oxidoreductases in microorganisms. Such enzymes provide a basis for elucidating the molecular mechanisms of enzyme-mediated asymmetric reactions involving stereo-recognition between proteins and chiral molecules, and mechanisms of electron transfer between functional groups of chiral molecules and key amino acid residues in enzymes. Apart from their unique value in studies of mechanisms of stereospecific oxidoreduction reactions, these novel carbonyl reductases of anti-Prelog stereopreference, have multiple potential uses in industrial applications to produce chiral alcohols useful as intermediates in fine chemical synthesis.

In some embodiments of the invention, the carbonyl reductase can catalyze asymmetric reduction of 2-hydroxyacetophenone into (S)-1-phenyl-1,2-ethanediol (PED) (Nie et al., Appl. Environ. Microbiol., 73, 3759-3764 (2007)), a versatile chiral building block for the synthesis of pharmaceuticals, agrochemicals, and liquid crystals. PED is also a precursor for the production of chiral biphosphines and a chiral initiator for stereoselective polymerization (Iwasaki et al., Org. Lett., 1, 969-972 (1999); Liese et al., Biotechnol. Bioeng., 51, 544-550 (1996)).

In some embodiments, the carbonyl reductase can catalyze the reduction of a compound that comprises an aryl ketone, an aliphatic ketone, an α-ketoester, or β-ketoester. In some embodiments, the carbonyl reductase catalyzes the reduction of an aryl ketone. In some embodiments, the carbonyl reductase catalyzes the reduction of an aliphatic ketone. In some embodiments, the carbonyl reductase catalyzes the reduction of an α-ketoester. In some embodiments, the carbonyl reductase catalyzes the reduction of β-ketoester.

The term "nucleic acid" refers to deoxyribonucleotides or ribonucleotides and polymers thereof in either single or double stranded form, made of monomers (nucleotides) containing a sugar, phosphate and a base that is either a purine or pyrimidine. Unless specifically limited, the term encompasses known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues.

The term "nucleotide sequence" refers to a polymer of DNA or RNA which can be single-stranded or double-stranded, optionally containing synthetic, non-natural or altered nucleotide bases capable of incorporation into DNA or RNA polymers. The terms "nucleic acid," "nucleic acid molecule," and "polynucleotide" are used interchangeably.

Certain embodiments of the invention encompass compositions that comprise isolated or substantially purified nucleic acid. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule is substantially free of other cellular material or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Thus, the determination of percent identity between any two sequences can be accomplished using a mathematical algorithm. Non-limiting examples of such mathematical algorithms are the algorithm of Myers and Miller (Myers and Miller, *CABIOS*, 4, 11 (1988)); the local homology algorithm of Smith et al. (Smith et al., *Adv. Appl. Math.*, 2, 482 (1981)); the homology alignment algorithm of Needleman and Wunsch (Needleman and Wunsch, *JMB*, 48, 443 (1970)); the search-for-similarity-method of Pearson and Lipman (Pearson and Lipman, *Proc. Natl. Acad. Sci. USA*, 85, 2444 (1988)); the algorithm of Karlin and Altschul (Karlin and Altschul, *Proc. Natl. Acad. Sci. USA*, 87, 2264 (1990)), modified as in Karlin and Altschul (Karlin and Altschul, *Proc. Natl. Acad. Sci. USA*, 90, 5873 (1993)).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program and GAP, BESTFIT, BLAST, FASTA, and TFASTA in the Wisconsin Genetics Software Package (available from Genetics Computer Group (GCG), 575 Science Drive, Madison, Wis., USA). Alignments using these programs can be performed using the default parameters. The CLUSTAL program is well described by Higgins et al. (Higgins et al., *CABIOS*, 5, 151 (1989)); Corpet et al. (Corpet et al., *Nucl. Acids Res.*, 16, 10881 (1988)); Huang et al. (Huang et al., *CABIOS*, 8, 155 (1992)); and Pearson et al. (Pearson et al., *Meth. Mol. Biol.*, 24, 307 (1994)). The ALIGN program is based on the algorithm of Myers and Miller, supra. The BLAST programs of Altschul et al. (Altschul et al., *JMB*, 215, 403 (1990)) are based on the algorithm of Karlin and Altschul supra.

Software for performing BLAST analyses is publicly available through the National Center for Biotechnology Information. In addition to calculating percent sequence identity, the BLAST algorithm also performs a statistical analysis of the similarity between two sequences. To obtain gapped alignments for comparison purposes, Gapped BLAST can be utilized. Alternatively, PSI-BLAST can be used to perform an iterated search that detects distant relationships between molecules. When utilizing BLAST, Gapped BLAST, PSI-BLAST, the default parameters of the respective programs (e.g., BLASTN for nucleotide sequences, BLASTX for proteins) can be used.

For purposes of the present invention, comparison of nucleotide sequences for determination of percent sequence identity to another sequence may be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore may not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) (i) The term "substantial identity" of polynucleotide sequences means that a polynucleotide comprises a sequence that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, or even at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, 80%, 90%, or even at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e) (ii) The term "substantial identity" in the context of a peptide indicates that a peptide comprises an amino acid sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, or even 95%, 96%, 97%, 98% or 99%, sequence identity to a reference sequence over a specified comparison window. In certain embodiments, optimal alignment is conducted using the homology alignment algorithm of Needleman and Wunsch (Needleman and Wunsch, *JMB*, 48, 443 (1970)). An indication that two peptide sequences are substantially identical is that one peptide is immunologically reactive with antibodies raised against the second peptide. Thus, a peptide is substantially identical to a second peptide, for example, where the two peptides differ only by a conservative substitution. Thus, certain embodiments of the invention provide amino acid sequences that are substantially identical to the amino acid sequences described herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point (Tm) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl (1984); $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), the SSC concentration is increased so that a higher temperature can be used. Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. For short nucleotide sequences (e.g., about 10 to 50 nucleotides), stringent conditions typically involve salt concentrations of less than about 1.5 M, less than about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2×(or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids that have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

In addition to the chemical optimization of stringency conditions, analytical models and algorithms can be applied to hybridization data-sets (e.g. microarray data) to improve stringency.

The invention will now be illustrated by the following non-limiting Example.

EXAMPLE 1

Anti-Prelog Stereospecific Carbonyl Reductases

Three open reading frames (ORFs) in the 960-kb contig005802 of *C. parapsilosis* have been discovered. These ORFs encode the stereospecific carbonyl reductase genes (scr1, scr2, and scr3). These ORFs have been cloned and expressed, and the encoded proteins purified to homogeneity and confirmed to function as stereospecific carbonyl reductases (SCR1, SCR2, and SCR3).

Figure 2:
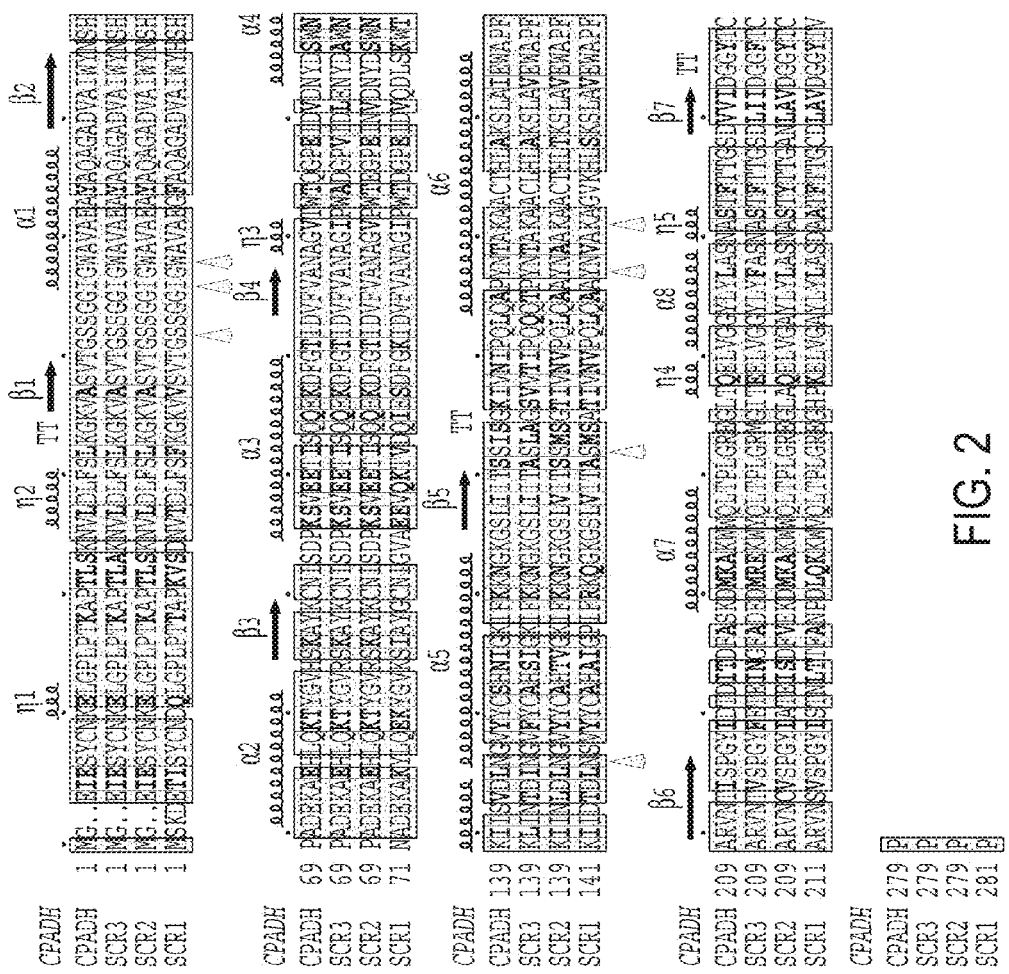
FIG. 2. Amino acid sequence alignment of CPADH (GenBank accession number DQ675534; SEQ ID NO:1), SCR1 (GenBank accession number FJ939565; SEQ ID NO:4), SCR2 (GenBank accession number FJ939563; SEQ ID NO:3), and SCR3 (GenBank accession number FJ939564; SEQ ID NO:2) from C. parapsilosis. Gaps in the aligned sequences are indicated by dashes. Identical amino acid residues are enclosed in boxes. The conserved sequences of the cofactor-binding motif Gly-X-X-X-Gly-X-Gly (SEQ ID NO:9) and the catalytic tetrad of Asn-Ser-Tyr-Lys (SEQ ID NO:10) in the majority of SDRs are marked with arrows.

Identification of Putative Stereospecific Carbonyl Reductases-Encoding Genes. Three ORFs, named here as scr1, scr2, and scr3 coding for putative stereospecific carbonyl reductases (SCRs) were identified. As shown in FIG. 1, these three ORFs, as well as the cpadh gene, locate in the 960-kb contig005802 of the *C. parapsilosis* genome. The scr1, scr2, and scr3 genes comprise 846, 840, and 840 bp, encoding polypeptides of 281, 279, and 279 amino acid residues with the calculated molecular masses of 30,061, 29,993, and 30,097 Da, respectively. Multiple sequence alignment of these four ORFs (FIG. 2) revealed high sequence identity between CPADH and SCR1 (68%), SCR2 (88%), and SCR3 (84%). Key active-site residues in the catalytic domain of the short-chain dehydrogenase/reductase (SDR) superfamily, including the cofactor-binding motif of Gly-x-x-x-Gly-x-Gly (x denotes any amino acid; SEQ ID NO:9) and the catalytic triad of Ser-Tyr-Lys (SEQ ID NO:11) are also found in SCR1, SCR2, and SCR3.

Figure 3:
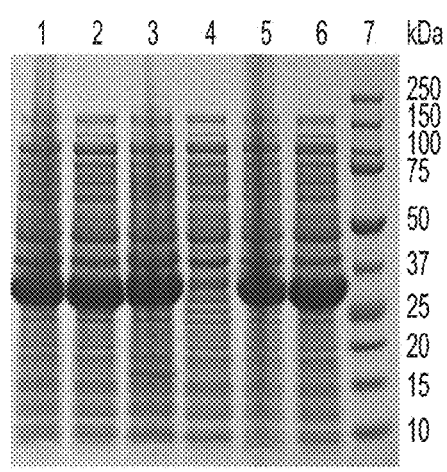
FIG. 3. Analysis of the overexpression of SCR1, SCR2, and SCR3. The proteins were separated on a 12% SDS-polyacrylamide gel and stained with Coomassie Brilliant Blue G-250. Lane 1, total protein for SCR1; Lane 2, soluble fraction for SCR1; Lane 3, total protein for SCR2; Lane 4, soluble fraction for SCR2; Lane 5, total protein for SCR3; Lane 6, soluble fraction for SCR3; Lane 7, molecular mass standard.

Cloning, Expression, and Purification of SCRs. From the nucleotide sequence of the ORFs, scr1, scr2, and scr3 were amplified by PCR from genomic DNA of *C. parapsilosis* CCTCC M203011, and the PCR products were inserted into pET21c vector by ligation-independent cloning to construct the recombinant plasmids. These three plasmids, pET21-SCR1, pET21-SCR2, and pET21-SCR3, were then transformed into expression host *E. coli* BL21(DE3) pMgK cells, and recombinant SCR1, SCR2, and SCR3 were produced in *E. coli* as fusion proteins containing a C-terminal His$_6$ tag (SEQ ID NO:12). All three recombinant enzymes were expressed at very high levels. Of them, SCR1 and SCR3 were expressed as soluble form at yields of 50 mg/l broth and 46 mg/l broth, respectively, while SCR2 has relatively low solubility with a yield of 5 mg/l broth (FIG. 3).

Figure 4:
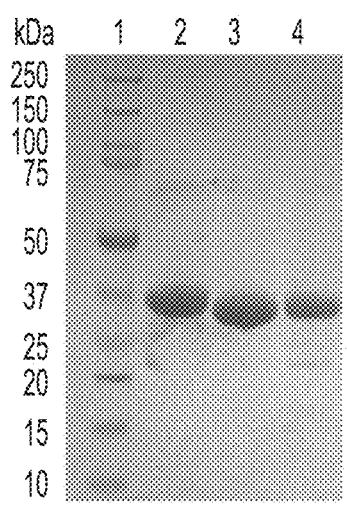
FIG. 4. SDS-PAGE analysis of purified enzymes. The purified proteins were resolved by SDS-PAGE on a 12% polyacrylamide gel and stained with Coomassie Brilliant Blue G-250. Lane 1, molecular mass standard; Lane 2, purified SCR1; Lane 3, purified SCR2; Lane 4, purified SCR3.

The three recombinant enzymes were purified to homogeneity as judged by Coomassie Brilliant Blue staining of SDS-PAGE (FIG. 4) by Ni affinity purification followed by gel filtration chromatography. The relative molecular mass of the SCR1 and SCR3 were estimated to be 124.6 kDa, and 123.4 kDa by analytic gel filtration and static light scattering using the same low salt buffer (Acton et al., *Methods Enzymol.*, 394, 210-243 (2005)), but SCR2 was detected as aggregated form. Since the relative molecular mass of the monomer of the recombinant enzymes should be around 30 kDa based on their amino acid composition, these results suggested that both SCR1 and SCR3 have tetrameric structures.

Catalytic Properties of Recombinant SCRs. The enzymatic activities of SCR1, SCR2, and SCR3 were investigated for reduction of 2-hydroxyacetophenone. Under the assay conditions, SCR1 gave the highest specific activity of 5.16 μmol/min mg protein, and SCR3 had the catalytic activity of 4.23 μmol/min mg protein, while SCR2 has a lower specific activity of 1.55 mol/min mg protein. In addition, the SCRs all displayed catalytic activity with NADPH as the coenzyme, but very low activities with NADH, indicating that these three enzymes are NADPH-dependent oxidoreductases.

Figure 5:
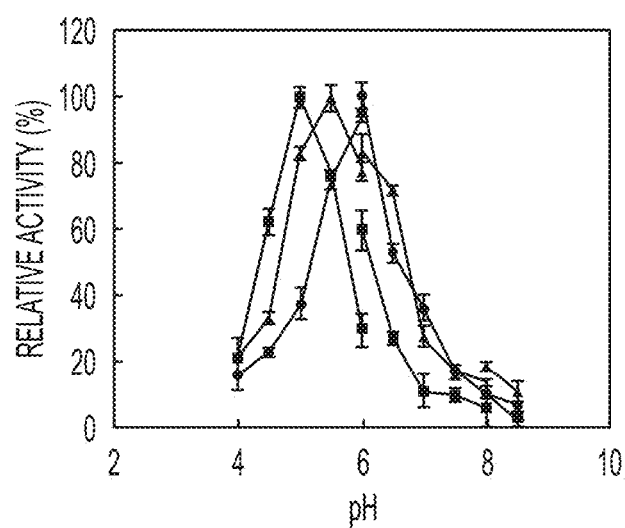
FIG. 5. pH dependence of SCR1, SCR2, and SCR3 catalyzing 2-hydroxyacetophenone reduction. The enzyme activities of SCR1 (squares), SCR2 (triangles), and SCR3 (circles) were measured in 0.1 M acetate buffer (pH 4.0 to 6.0) or 0.1 M sodium phosphate buffer (pH 6.0 to 8.0) or 0.1 M Tris-HCl buffer (pH 8.0 to 8.5) with 2-hydroxyacetophenone as the substrate and NADPH as the cofactor. Maximal enzyme activity observed was set as 100% relative activity for each enzyme.
Figure 6A:
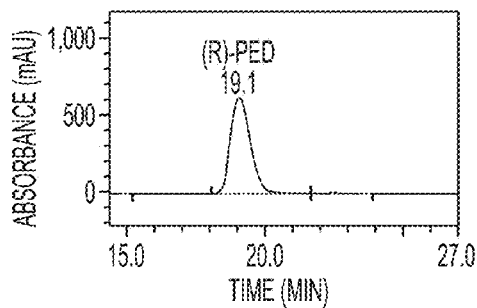
FIG. 6A-6E. Asymmetric reduction of 2-hydroxyacetophenone (2-HAP) to 1-phenyl-1,2-ethanediol (PED) enantiomer by SCR1, SCR2, and SCR3, respectively. (6A) Standard sample of (R)-PED. (6B) Standard sample of (S)-PED. (6C) SCR1 catalyzed asymmetric reduction of 2-HAP. (6D) SCR2 catalyzed asymmetric reduction of 2-HAP. (6E) SCR3 catalyzed asymmetric reduction of 2-HAP.
Figure 6B:
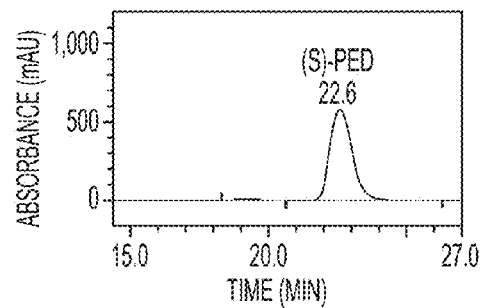
Figure 6C:
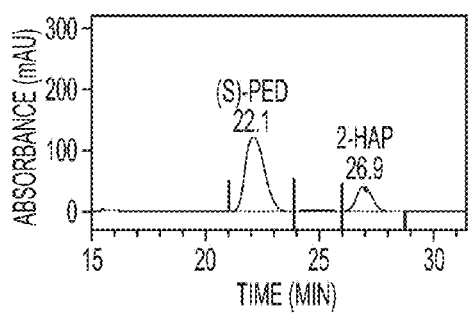
Figure 6D:
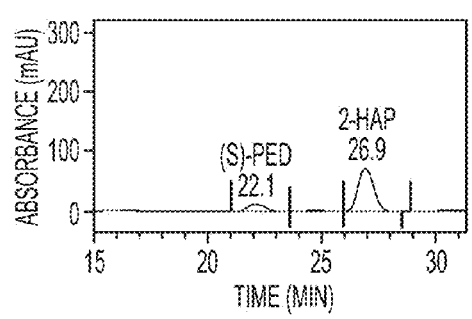
Figure 6E:
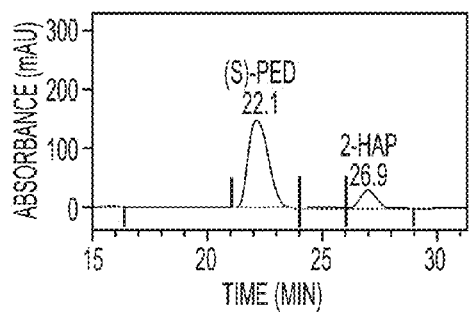

Since environmental pH value can have an influence on the stereochemistry of enzymatic reactions (Secundo and Phillips, *Enzyme Microb. Technol.*, 19, 487-492 (1996)), the effect of the reaction pH on the activities of SCRs catalyzing 2-hydroxyacetophenone reduction was also investigated. All three enzymes exhibited the highest activity at the pH ranging from 5.0 to 6.0 (FIG. 5). Subsequently, the enzymes were evaluated under their individual optimal pH, and apparent kinetic parameters were further measured by double reciprocal Lineweaver-Burk plots at various 2-hydroxyacetophenone concentrations with fixed NADPH concentrations. As shown in Table 1, for reduction of 2-hydroxyacetophenone, these three enzymes exhibited different kinetic parameters. The values are the average of three independent experiments.

TABLE 1

Activities and kinetic parameters for reduction of 2-hydroxyacetophenone (2-HAP) by SCR1, SCR2, SCR3, and CPADH, using NADPH as a cofactor

| Enzyme | pH[a] | Specific activity (μmol/min mg protein) | $K_m$ (mM) | $V_m$ (μmol/min mg protein) |
|---|---|---|---|---|
| SCR1 | 5.0 | 5.16 | 9.83 | 42.0 |
| SCR2 | 5.5 | 1.55 | 4.81 | 8.83 |
| SCR3 | 6.0 | 4.23 | 4.68 | 32.3 |
| CPADH | 4.5 | 2.70 | 5.83 | 18.3 |

[a] Activity assay was carried out at the optimum pH for each enzyme.

Stereoselectivity to Prochiral Carbonyl Group. Using 2-hydroxyacetophenone as the substrate, optically pure 1-phenyl-1,2-ethanediol (PED) of (S)-enantiomer (>99% e.e.) was produced by each of SCR1, SCR2, and SCR3, respectively (FIG. 6). These three enzymes catalyze asymmetric reduction of prochiral carbonyl compounds and are all (S)-specific carbonyl reductase toward 2-hydroxyacetophenone. Of them, however, SCR2 is not as efficient as the other two enzymes, corresponding to its lower activity. These data demonstrate that the SCR1, SCR2, and SCR3 enzymes are anti-Prelog-type stereospecific carbonyl reductases (Manzocchi et al., *J. Org. Chem.*, 53, 4405-4407 (1988); Nie et al.,

*Appl. Environ. Microbiol.,* 73, 3759-3764 (2007); Prelog, *Pure Appl. Chem.,* 9, 119-130 (1964)).

Figures 7A, 7B, 7C, 7D:
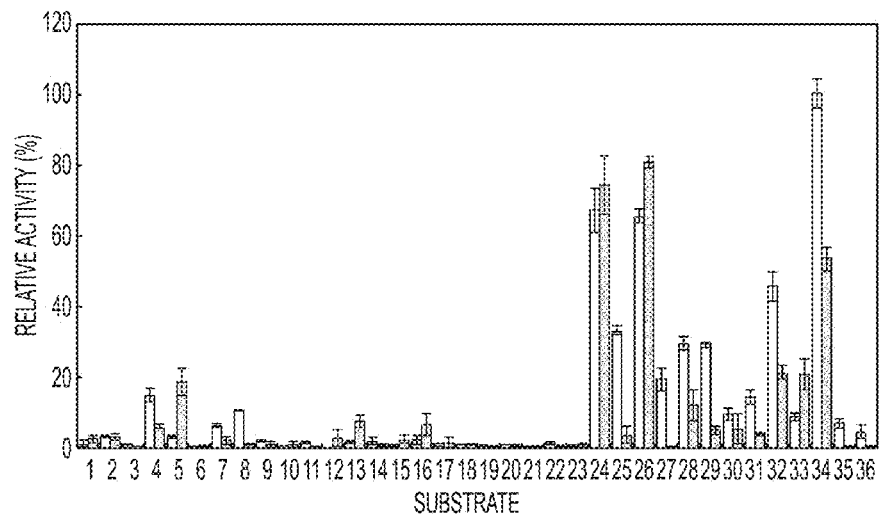
FIG. 7A-7D. Substrate specificity of SCR1 and SCR3. The enzyme activities of SCR1 (open bars) and SCR3 (shaded bars) (7A) to various substrates (7B-7D) were measured as described herein. Maximal enzyme activity observed was set as 100% relative activity for the enzymes to various substrates.

Substrate Specificity. Since SCR1 and SCR3 showed distinct (S)-specific carbonyl-reducing activity, the substrate specificity of these two enzymes was further examined to various carbonyl compounds including aryl ketones, aliphatic ketones, α- and β-ketoesters. As shown in FIG. 7, on the one hand, both the enzymes exhibited higher catalytic activity to ketoesters than to alkyl and aromatic ketones; on the other hand, the enzymes showed diversity on specificity to aryl ketones and ketoesters, respectively. For both substituted acetophenone and 2-hydroxyacetophenones derivatives, bearing chloro or methyl at various positions of the phenyl ring, the ortho substituents were poor substrates for these enzymes, indicating that the substitution at ortho position might have steric influence on the hydrogen attack from electron donator NADPH to the carbonyl group and significant influence on the reactivity of the enzymes. However, SCR3 was more specific to p-Cl-2-hydroxyacetophenone, while SCR1 had higher activity to m-Cl-2-hydroxyacetophenone. For ketoesters, the enzymes both exhibited high activity to those with small groups, but compared with SCR3, SCR1 was more active to bulky ketoesters with phenyl ring and generally showed higher activities to β-ketoesters. Worth to note, among the tested ≠2-ketoesters, SCR1 preformed the highest activity for the reduction of ethyl 4-chloro-3-oxobutyrate, which affords ethyl 4-chloro-3-hydroxybutyrate, an important pharmaceutical intermediate (Thayer, *Chem. Eng. News,* 84, 26-27 (2006).

Materials and Methods

Materials. *C. parapsilosis* strain CCTCC M203011 was obtained from the China Center for Type Culture Collection (CCTCC, Wuhan, China). *Escherichia coli* XL-10 gold cells were used for gene cloning and plasmid preparation, and *E. coli* BL21 (DE3) pMgK competent cells, a rare codon-enhanced strain, were used for gene expression. High-fidelity PCR kit including DNA polymerase was purchased from FINNZYMES (Finland). The plasmid pET21c was obtained from Novagen (USA). (R)- and (S)-1-phenyl-1,2-ethanediol, all the aliphatic ketones and ketone esters, aryl ketones including acetophenone and its derivatives, 2-hydroxyacetophenone, propiophenone, butyrophenone, valerophenone, hexanophenone, and coenzymes including NAD(P)H and NAD(P)$^+$ were purchased from Sigma-Aldrich (USA). All other 2-hydroxyacetophenone derivatives including o-Cl-2-hydroxyacetophenone, m-Cl-2-hydroxyacetophenone, p-Cl-2-hydroxyacetophenone, and p-CH$_3$O-2-hydroxyacetophenone were prepared using the method described by Itsuno (Itsuno et al., *J. Chem. Soc. Perkin Trans. 1,* 2039-2044, (1985)). All other chemicals used in this work were of analytical grade and commercially available.

Cloning and Expression of Genes Encoding Stereospecific Reductases. The genes encoding SCR1, SCR2, and SCR3 were amplified by polymerase chain reaction from *C. parapsilosis* genomic DNA. PCR-amplified DNA products were purified by QIAquick PCR Purification Kit (QIAGEN, USA) and inserted into pET21c expression vector (Novagen, USA) by ligation-independent cloning (LIC) using In-Fusion PCR Cloning Kit (Clontech, USA) for construction of recombinant plasmids. The infusion reaction mixtures were used to transform *E. coli* XL-10 gold cells. The plasmids isolated from these transformants were verified by DNA sequence analysis using BigDye Terminator cycle sequencing kit and an ABI PRISM 310 Genetic Analyzer (Applied Biosystems, USA). The plasmids with the correct inserts, pET21-SCR1, pET21-SCR2, and pET21-SCR3, were transformed into *E. coli* BL21(DE3) pMgK competent cells for the production of SCRs. These plasmids provide SCRs with a six-His tag (SEQ ID NO:12) fused at the C-terminus.

*E. coli* BL21 (DE3) pMgK transformants were cultivated at 37° C. in Luria broth (LB) medium in the presence of ampicillin (100 µg/ml) and kanamycin (50 µg/ml). When the optical density of the culture at 600 nm reached 0.6, the temperature was changed to 17° C. and isopropyl-β-D-thiogalactopyranoside (IPTG) was added to the culture to give a final concentration of 1 mM for induction of gene expression. After an additional incubation of 20 h at 17° C., cells harvested by centrifugation were disrupted by sonication, and expressions of the recombinant proteins were analyzed by sodium dodecyl sulfate-polyacrylamide gel electrophoresis (SDS-PAGE).

Purification of Recombinant Enzymes. The cells were suspended in binding buffer (20 mM Tris-HCl, pH7.5, 0.3 M NaCl, 40 mM imidazole, 1× protease inhibitors, 1 mM Tris (2-carboxyethyl)phosphine (TCEP)) and disrupted on ice by sonication. The supernatant of the cell lysate was collected by centrifugation at 26,000×g for 40 min at 4° C. and purified by an AKTAxpress system using HisTrap HP affinity column followed by Superdex 75 gel filtration column (GE Healthcare, USA), and the purified fractions were exchanged into low salt buffer (10 mM Tris-HCl, pH 7.5, 0.1 M NaCl, 0.02% NaN$_3$, 5 mM D,L-dithiothreitol) (Acton et al., *Methods Enzymol.,* 394, 210-243 (2005)). The final recombinant enzymes were purified with an apparent homogeneity on sodium dodecyl sulfate-polyacrylamide gel electrophoresis (SDS-PAGE) with 12% polyacrylamide gels. Their molecular masses were measured by matrix-assisted laser desorption ionization time-of-flight (MALDI-TOF) mass spectrometry (Applied Biosystems, USA), and their oligomerization states were determined by analytic gel filtration using Agilent 1200 seriers HPLC system followed by static light scattering (Wyatt Technology, USA). These final preparations of purified SCRs were used in all of the experiments in this study.

Enzyme Assays. Carbonyl reductase activity was measured by a continuous spectrophotometric assay using 2-hydroxyacetophenone as a substrate. One unit of enzyme activity was defined as the amount of enzyme catalyzing the oxidation of 1 µmol NAD(P)H per min under the assay conditions. The standard assay mixture for the enzyme activity comprised of 0.1 M potassium phosphate buffer (pH 6.5), 0.3 mM NAD(P)H, 0.7 mM 2-hydroxyacetophenone and appropriate enzyme in a total volume of 100 µl. The decrease in the amount of the coenzyme was measured spectrophotometrically at 340 nm (extinction coefficient [ε]=6.22 mM$^{-1}$ cm$^{-1}$). Protein concentration was determined using Bradford reagents (Bio-Rad) with bovine serum albumin as a standard. The pH dependence of enzyme activity was determined over a pH range of 4.0 to 8.5 using the following buffers: 0.1 M acetate (pH 4.0 to 6.0), 0.1 M sodium phosphate (pH 6.0 to 8.0) and 0.1 M Tris-HCl (pH 8.0 to 8.5).

The substrate specificity of SCRs was investigated under the same conditions as described above. Various carbonyl compounds including aryl ketones, aliphatic ketones, α- and β-ketone esters were used as the substrates with the cofactor of NADPH.

Asymmetric Reduction and Stereoselectivity Assay. Asymmetric reduction of 2-hydroxyacetophenone by the purified enzymes were carried out at 30° C. for 6 h with shaking in a reaction mixture comprising 0.1 M potassium phosphate buffer (pH 6.5), 1 g/l 2-hydroxyacetophenone, NADPH (7 mM) and 0.5 mg of the purified enzyme in a total volume of 0.5 ml. The reaction products were extracted with ethyl acetate and the organic layer was used for analysis. The optical purity of reaction products were analyzed by HPLC using a Chiralcel OB-H column (4.6×250 mm, Daicel Chemical Ind., Ltd., Japan). Enantiomers were eluted with hexane and 2-propanol (9:1) at a flow rate of 0.5 ml/min. The effluent was monitored at 215 nm, and the areas under each peak were integrated (Nie et al., *Org. Process Res. Dev.*, 8, 246-251 (2004)).

Nucleotide Sequence Accession Number. The nucleotide sequence for the stereospecific carbonyl reductase genes scr1, scr2, and scr3 have been deposited in the GenBank database under accession numbers FJ939565 (SEQ ID NO:8), FJ939563 (SEQ ID NO:7), and FJ939564 (SEQ ID NO:6), respectively.

All publications, patents and patent applications cited herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A method of reducing a carbonyl substrate, comprising contacting the substrate with a purified polypeptide having carbonyl reductase activity, the sequence of which comprises an amino acid sequence that has at least 80% sequence identity to SEQ ID NO:4, at least 95% sequence identity to SEQ ID NO:3 or at least 90% sequence identity to SEQ ID NO:2, in conditions suitable to catalyze the reduction of the carbonyl substrate.

2. The method of claim 1, wherein the reduction takes place in the presence of a coenzyme.

3. The method of claim 2, wherein the coenzyme is NADPH.

4. The method of claim 1, wherein the carbonyl substrate comprises an α-ketoester, a β-ketoester, an aryl ketone or an aliphatic ketone.

5. The method of claim 4, wherein the carbonyl substrate comprises an α-ketoester.

6. The method of claim 5, wherein the α-ketoester is methyl pyruvate, methyl phenylglyoxylate, ethyl pyruvate or ethyl benzoylformate.

7. The method of claim 4, wherein the carbonyl substrate comprises a β-ketoester.

8. The method of claim of claim 7, wherein the β-ketoester is ethyl trifluoroacetoacetate, methyl acetoacetate, methyl 3-oxovalerate, methyl 4-fluorobenzoylacetate, ethyl acetoacetate, ethyl 3-oxovalerate, ethyl 4-chloroacetoacetate, ethyl benzoylacetate, or ethyl 3,4-dimethoxybenzoylacetate.

9. The method of claim 4, wherein the carbonyl substrate comprises an aryl ketone.

10. The method of claim 9, wherein the aryl ketone is 2-hydroxyacetophenone, or a derivative thereof.

11. The method of claim 10, wherein the aryl ketone is 2'-chloro-2-hydroxyacetophenone, 3'-chloro-2-hydroxyacetophenone, 4'-chloro-2-hydroxyacetophenone or 4'-methoxy-2-hydroxyacetophenone.

12. The method of claim 4, wherein the carbonyl substrate comprises an aliphatic ketone.

13. The method of claim 12, wherein the aliphatic ketone is 2-butanone, 2-pentanone, 2-hexanone, 2-heptanone, 2-octanone or 2-methyl-3-pentanone.

14. The method of claim 1, wherein the carbonyl substrate is ethyl 4-chloro-3-oxobutyrate.

15. The method of claim 1, wherein the reduction takes place at pH ranging from 5.0 to 6.0.

16. The method of claim 1, wherein the amino acid sequence has at least 85% sequence identity to SEQ ID NO:4.

17. The method of claim 1, wherein the amino acid sequence has at least 90% sequence identity to SEQ ID NO:4.

18. The method of claim 1, wherein the amino acid sequence has at least 95% sequence identity to SEQ ID NO:4.

19. The method of claim 1, wherein the amino acid sequence has at least 99% sequence identity to SEQ ID NO:3.

20. The method of claim 1, wherein the amino acid sequence has at least 99% sequence identity to SEQ ID NO:2.

21. The method of claim 1, wherein the amino acid sequence has at least 95% sequence identity to SEQ ID NO:2.

22. The method of claim 1, wherein the amino acid sequence comprises SEQ ID NO:4, SEQ ID NO:3 or SEQ ID NO:2.

23. The method of claim 1, wherein the amino acid sequence consists of SEQ ID NO:4, SEQ ID NO:3 or SEQ ID NO:2.

24. The method of claim 1, wherein the amino acid sequence comprises SEQ ID NO:9, SEQ ID NO:10 and/or SEQ ID NO:11.

* * * * *